(12) United States Patent
Shechter et al.

(10) Patent No.: US 8,279,997 B2
(45) Date of Patent: Oct. 2, 2012

(54) DYNAMIC COMPUTED TOMOGRAPHY IMAGING

(75) Inventors: Gilad Shechter, Haifa (IL); Asher Gringaus, Nesher (IL); Yoav Bar, Haifa (IL); Guy Lavi, Avichail (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 896 days.

(21) Appl. No.: 12/302,108

(22) PCT Filed: May 9, 2007

(86) PCT No.: PCT/US2007/068539
§ 371 (c)(1),
(2), (4) Date: Nov. 24, 2008

(87) PCT Pub. No.: WO2007/140094
PCT Pub. Date: Dec. 6, 2007

(65) Prior Publication Data
US 2009/0290774 A1 Nov. 26, 2009

Related U.S. Application Data

(60) Provisional application No. 60/803,260, filed on May 26, 2006.

(51) Int. Cl.
*A61B 6/00* (2006.01)
*G06K 9/00* (2006.01)
(52) U.S. Cl. .................. 378/8; 378/4; 382/131
(58) Field of Classification Search .................. 382/131; 378/8
See application file for complete search history.

(56) References Cited

U.S. PATENT DOCUMENTS

| | | | | |
|---|---|---|---|---|
| 5,751,782 | A * | 5/1998 | Yoshitome | 378/98.5 |
| 5,991,356 | A * | 11/1999 | Horiuchi et al. | 378/8 |
| 6,243,437 | B1 * | 6/2001 | Hu et al. | 378/8 |
| 6,370,217 | B1 * | 4/2002 | Hu et al. | 378/8 |
| 6,426,990 | B1 * | 7/2002 | Cesmeli | 378/8 |
| 6,480,560 | B2 * | 11/2002 | Hsieh | 378/8 |
| 6,556,697 | B1 * | 4/2003 | Bruder et al. | 382/131 |
| 6,639,965 | B1 * | 10/2003 | Hsieh et al. | 378/8 |
| 6,775,346 | B2 * | 8/2004 | Heuscher et al. | 378/4 |
| 6,925,141 | B2 * | 8/2005 | Bruder et al. | 378/8 |
| 7,596,204 | B2 * | 9/2009 | Ziegler et al. | 378/8 |

(Continued)

FOREIGN PATENT DOCUMENTS
EP 1394747 A1 3/2004

OTHER PUBLICATIONS

Brady et al., Interactive Volume Navigation, IEEE Transactions on Visualization and Computer Graphics, Jul.-Sep. 1998, pp. 243-256, vol. 4, No. 3, IEEE.

(Continued)

*Primary Examiner* — Alexander H Taningco

(57) ABSTRACT

Projection data (302) acquired during a tomographic examination of a periodically moving object is used to reconstruct a plurality of image layers (308). The image layers (308) are combined to generate image data at a desired phase of motion. To generate a weighting function used to combine the image layers, a reference weighting function (512) is generated at the desired phase. The image layers (308) are weighted to approximate the first weighting function (312). The number of image layers and the size of a sub-region of interest are advantageously selected so that the various image layers can be stored in a relatively high speed memory portion of a computer.

20 Claims, 6 Drawing Sheets

U.S. PATENT DOCUMENTS

| | | | |
|---|---|---|---|
| 7,889,901 B2* | 2/2011 | Bontus et al. | 382/128 |
| 2003/0002616 A1* | 1/2003 | Cesmeli | 378/8 |
| 2003/0072419 A1* | 4/2003 | Bruder et al. | 378/210 |
| 2004/0131140 A1* | 7/2004 | Bruder et al. | 378/4 |
| 2004/0146137 A1* | 7/2004 | Bruder et al. | 378/4 |
| 2005/0111622 A1* | 5/2005 | Bruder et al. | 378/95 |
| 2005/0113665 A1 | 5/2005 | Mohr et al. | |
| 2005/0276372 A1 | 12/2005 | Bruder et al. | |
| 2007/0053483 A1* | 3/2007 | Nagata et al. | 378/8 |

OTHER PUBLICATIONS

Hong et al., ECG-gated Reconstructed Multi-Detector Row CT Coronary Angiography: Effect of Varying Trigger Delay on Image Quality, Radiology, 2001, pp. 712-717, RSNA.

Bruder et al., Segmented Cardiac Volume Reconstruction—A Novel Reconstruction Scheme for Multislice Cardiac Spiral CT, presented at the The Sixth International Meeting on Fully Three-Dimensional Image Reconstruction in Radiology and Nuclear Medicine, Oct.-Nov. 2001, 4 pages.

Stierstorfer, et al., Segmented Multiple Plan Reconstruction—A Novel Approximate Reconstruction Scheme for Multislice Spiral CT, Physics in Medicine and Biology, Aug. 7, 2002, 3 pages, vol. 47, No. 15, presented at the Sixth International Meeting on Fully Three-Dimensional Image Reconstruction on Radiology and Nuclear Medicine.

Grass et al., Helical Cardiac Cone Beam Reconstruction Using Retrospective ECG Gating, Physics in Medicine and Biology, 2003, pp. 3069-3084, vol. 48, Institute of Physics Publishing.

Saito et al., Real-Time Four-dimensional Imaging of the Heart with Multi-Detector Row CT, Radiographics, 2003, published on line Oct. 14, 2002, 6 pages, RSNA, http://radiographics.rsnajnls.org/cgi/content/full/23/1/e8.

Schoepf et al., CT of Coronary Artery Disease, Radiology, Jul. 2004, p. 18-37, vol. 232, No. 1, RSNA.

Blobel et al., Optimization of Temporal and Spatial Resolution of Cardiac CT Diagnostics, Toshiba Medical Systems Journal Visions, 2004, pp. 12-17, No. 05, Toshiba.

Bruder et al., Dynamic Cardiac CT Imaging Using Detectors with Large Cone Angle, presented at the Eighth International Meeting on Fully Three-Dimensional Image Reconstruction in Radiology and Nuclear Medicine, Jul. 9, 2005, pp. 405-408.

Hudson, H. M., et al.; Accelerated Image Reconstruction Using Ordered Subsets of Projection Data; 1994; IEEE Trans. on Medical Imaging; 13(4)601-609.

Manzke, R., et al.; Artifact Analysis and Reconstruction Improvement in Helical Cardiac Cone Beam CT; 2004; IEEE Trans. on Medical Imaging; 23(9)1150-1164.

Nielsen, T., et al.; Cardiac cone-beam CT volume reconstruction using ART; 2005; Med. Phys.; 32(4)851-860.

* cited by examiner

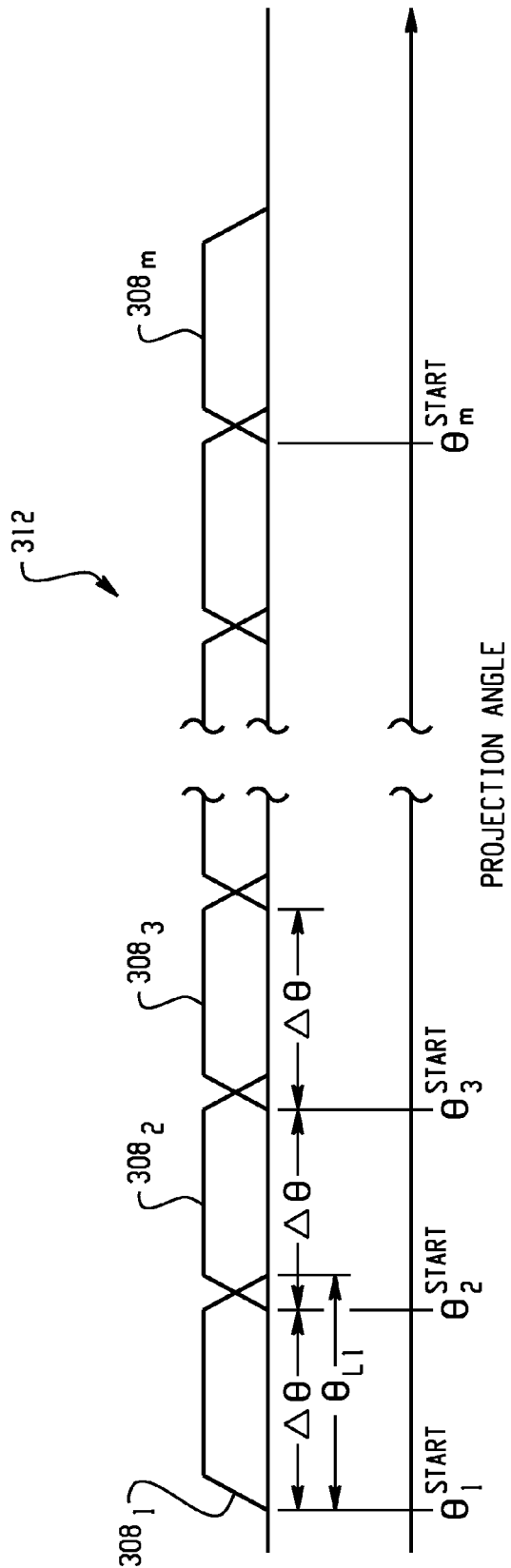

DYNAMIC COMPUTED TOMOGRAPHY IMAGING

CROSS REFERENCE TO RELATED APPLICATIONS

This application claims the benefit of U.S. provisional application Ser. No. 60/803,260 filed May 26, 2006, which is incorporated herein by reference.

The present invention relates to computed tomography (CT) imaging. It finds application to cardiac and other applications where it is desirable to improve the visualization of moving structures.

Recent developments in CT technology, such as increased gantry rotation speeds and the introduction and acceptance of multi-slice scanners, have opened new applications for CT imaging. One such application is that of cardiac imaging, and more particularly the visualization of the coronary arteries.

One particularly challenging aspect of cardiac imaging is obtaining volumetric data with the temporal resolution needed to effectively visualize the beating heart. See, e.g., Blobel, et al., *Optimization of Temporal and Spatial Resolution for Cardiac CT Diagnostics* (2004); Shoepf, et al., *CT of Coronary Artery Disease, Radiology* 2004: 232:18-32 (2004).

One technique for performing gated cardiac reconstruction is the extended cardiac reconstruction (ECR) method. See Grass, et al., *Helical Cardiac Cone Beam Reconstruction Using Retrospective ECG Gating*, Phys. Med. Biol. 48 (2003) 3069-3084. The ECR method is an approximate helical cone beam reconstruction method based on 3D filtered backprojection. Within this framework, a retrospective cardiac gating scheme restricts the temporal information to a certain cardiac motion state of interest. Redundancy of the data is achieved using a low pitch helical reconstruction mode.

More particularly, the ECR technique is based on the wedge method for helical cone beam reconstruction, which applies fan beam to parallel beam rebinning prior to cosine weighting, filtering and 3D back projection of the cone beam data. In addition to the geometric weighting factors inherent in the reconstruction geometry, the ECR method also includes a weighting function based on an illumination window, which is a result of the acquisition geometry. The method also includes a cardiac weighting function which is used to determine the part of the projection data in the temporal domain which is used to reconstruct an image volume image for a desired cardiac phase. Prior to back projection, the illumination weighting function and the cardiac weighting function are combined for each voxel in the volume using a normalization approach.

While an effective cardiac reconstruction technique, the ECR method has required a new backprojection for each cardiac phase to be visualized. As the backprojection step is computationally expensive, the ECR method is not well suited to applications where relatively rapid, interactive visualization of volumetric data at a plurality of cardiac phases is desired.

In another technique, the stream of acquisition data has been subdivided into data segments having an angular extent less than that required to form a complete tomographic data set. The data segments are in turn reconstructed to form a stream of segment images. Temporal rebinning has then been applied to the image data, which are then added to form the volumetric data. See Bruder, et al., *Dynamic Cardiac CT Imaging Using Detectors with Large Cone Angle*, Fully 3D Image Reconstruction in Radiology and Nuclear Medicine (2005).

While this approach has avoided the need to recalculate the image volume for each user selected cardiac phase, the cardiac phase can only be adjusted within a discrete temporal grid, which is a function of the angular extent of the image segments. Moreover, adding the segment images to obtain a full volumetric image of the heart at the re-selected phase has required a large amount of writing to the hard disc of the computer. Consequently, the technique does not allow the rapid, interactive visualization of the volumetric data at an arbitrary cardiac phase.

Aspects of the present invention address these matters, and others.

According to a first aspect of the present invention, a method includes using projection data acquired during a tomographic examination of a periodically moving object to reconstruct a plurality of image layers, combining the image layers to generate first image data indicative of the object at an arbitrary first motion phase, and displaying a human readable image indicative of the first image data. The image layers are generated from projection data segments having an angular extent less than that which is required to provide a complete tomographic data set.

According to another aspect of the invention, an apparatus includes means for using projection data acquired during a tomographic examination of a periodically moving object to reconstruct a plurality of image layers, means for combining the image layers to generate first image data indicative of the object at an arbitrary first motion phase, and means for displaying a human readable image indicative of the first image data. The image layers are generated from projection data segments having an angular extent less than that which is required to provide a complete tomographic data set.

According to another aspect of the present invention, a method includes using projection data acquired during a CT examination of a periodically moving object to reconstruct a plurality of image layers, combining the image layers according to a first weighting function to generate first image data indicative of the object at a first motion phase, displaying a human readable image indicative of the first image data, combining the image layers according to a second weighting function so as to generate second image data indicative of the object at a second motion phase, and generating a human readable image indicative of the object at the second motion phase. The image layers are generated from a plurality of angularly displaced projection data segments. The image layers are also displaced by a first angular displacement and the first and second motion phases are separated by an angular distance which is less than the first angular displacement.

According to another aspect, a computer readable storage medium carries instructions which, when executed by a computer, cause the computer to carry out a method including the steps of using projection data acquired during a tomographic examination of a periodically moving object to generate a plurality of image layers, generating a first angularly varying reference weighting function, weighting the image layers so that the weighting applied to the image layers approximates the first weighting function, combining the weighted image layers to generate first volumetric data indicative of the object, and generating a human readable image indicative of the first volumetric data.

Still other advantages and benefits will be appreciated by those skilled in the art upon reading and understanding the appended description.

Figure 3B:
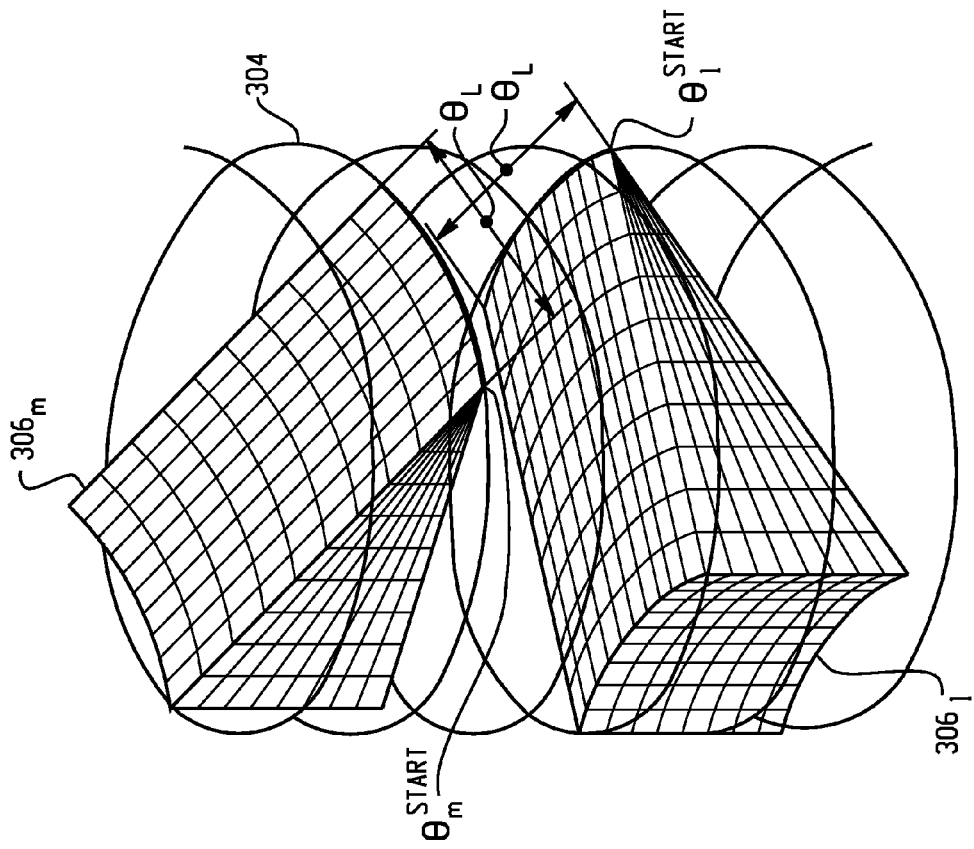
Figure 3A:
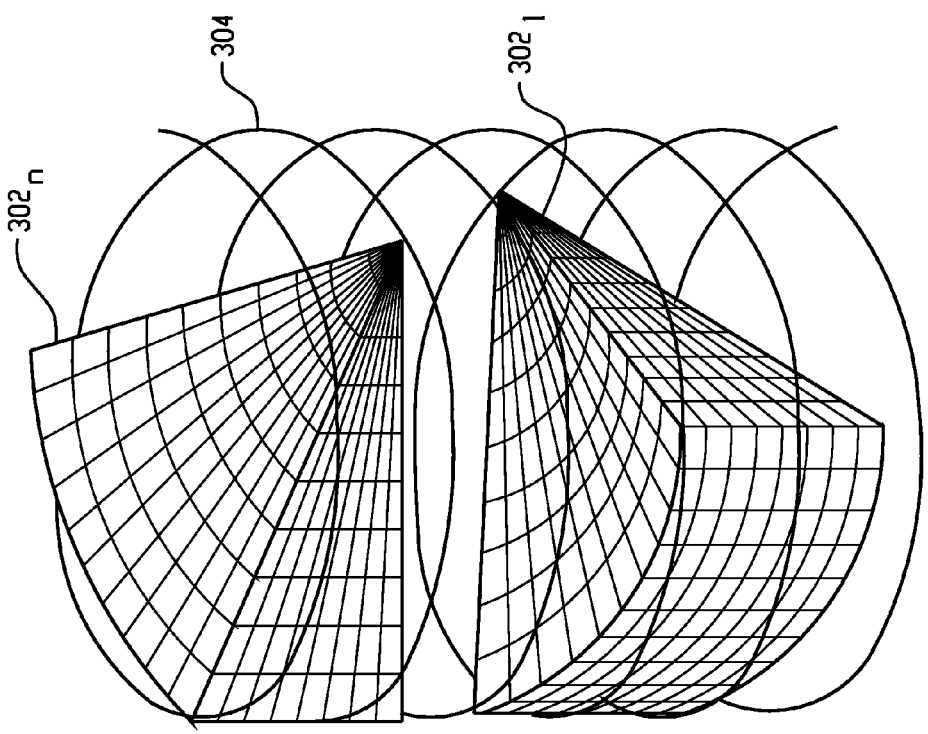

FIGS. 3A, 3B, and 3C depicts aspects of a technique for generating image layers.

Figure 4:
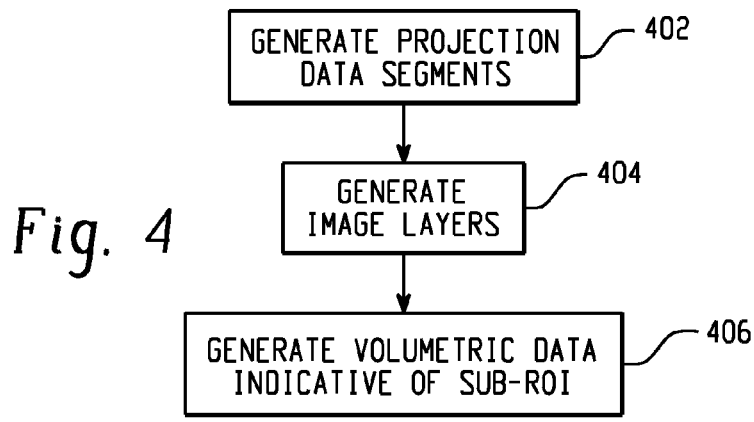

FIG. 4 depicts steps in generating image layers.

Figure 5:
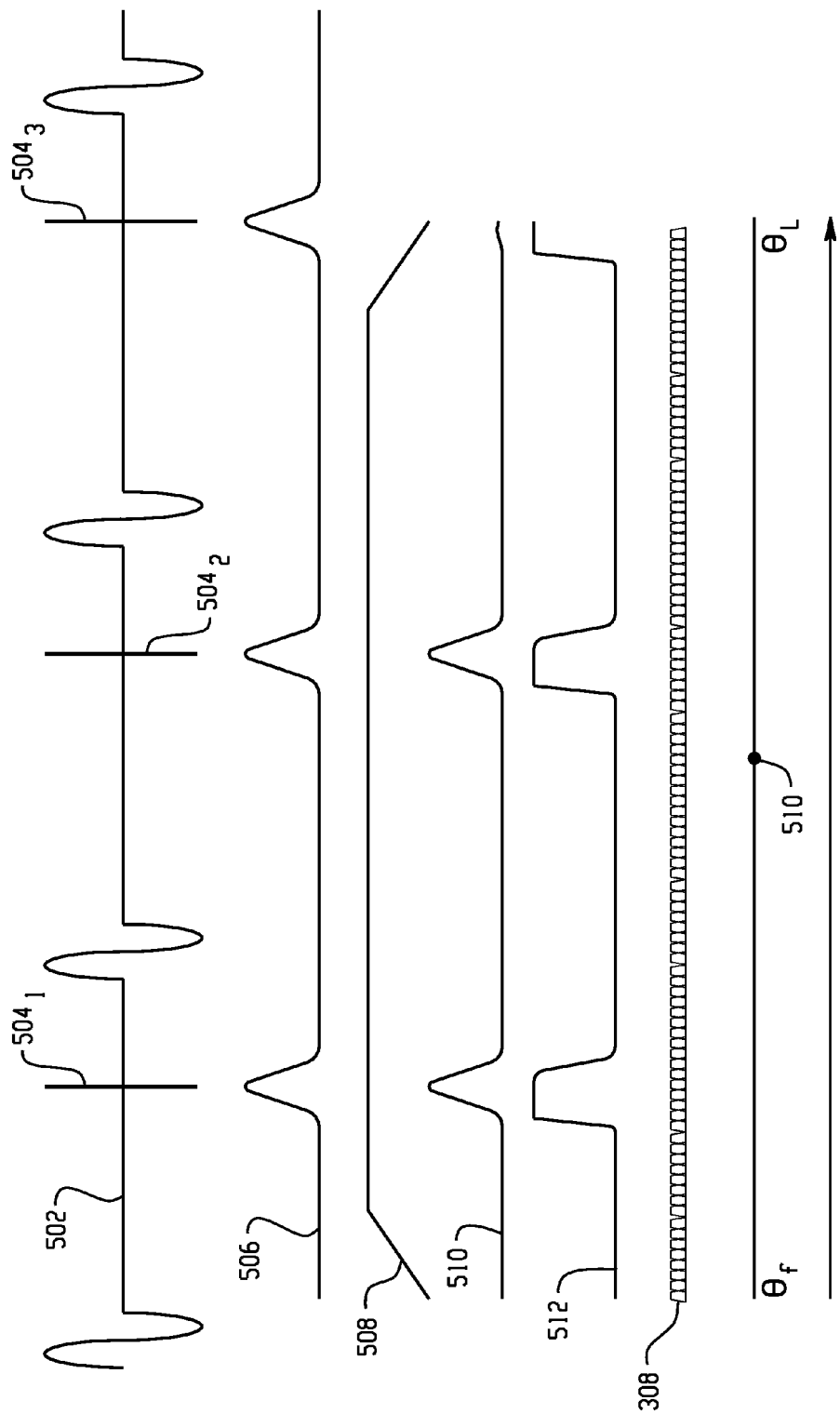

FIG. 5 depicts aspects of a technique for generating an image layer weighting function.

Figure 6:
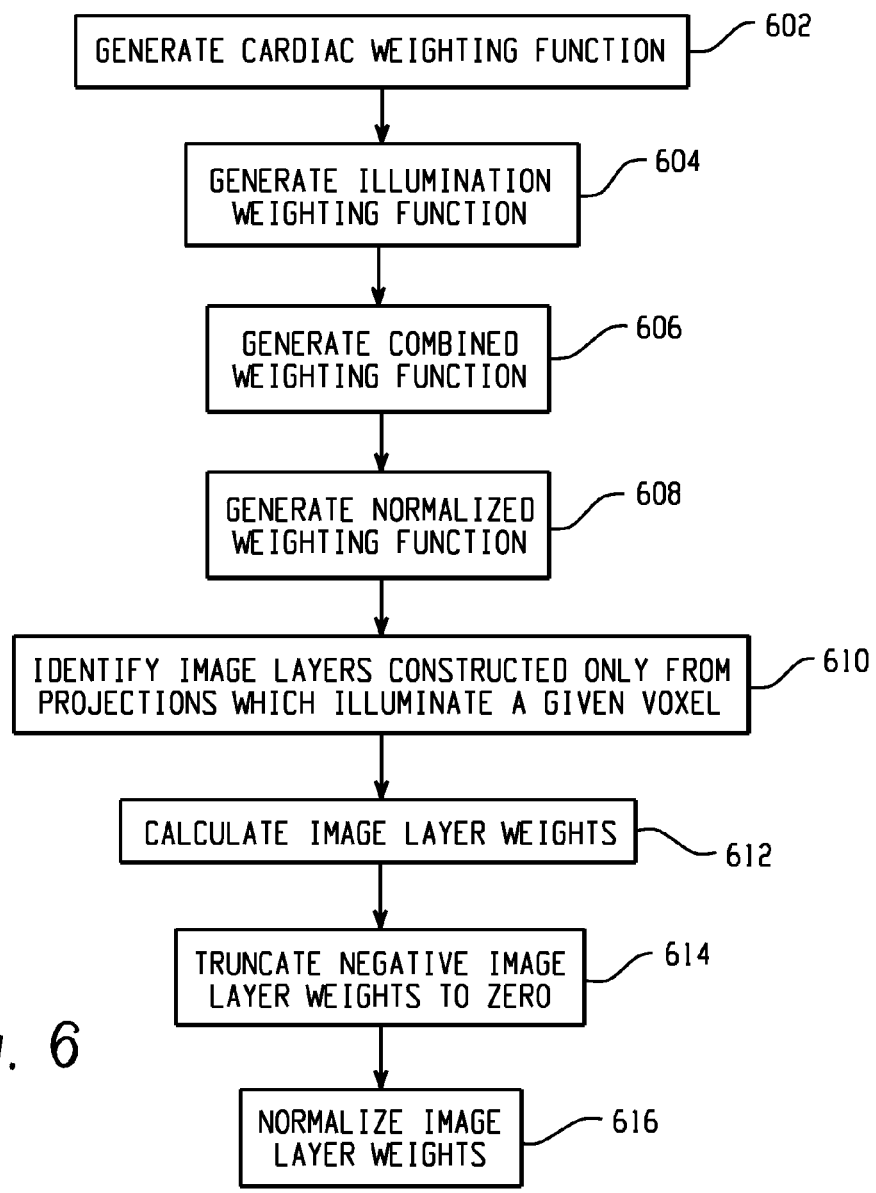

FIG. 6 depicts steps in generating an image layer weighting function.

Figure 1:
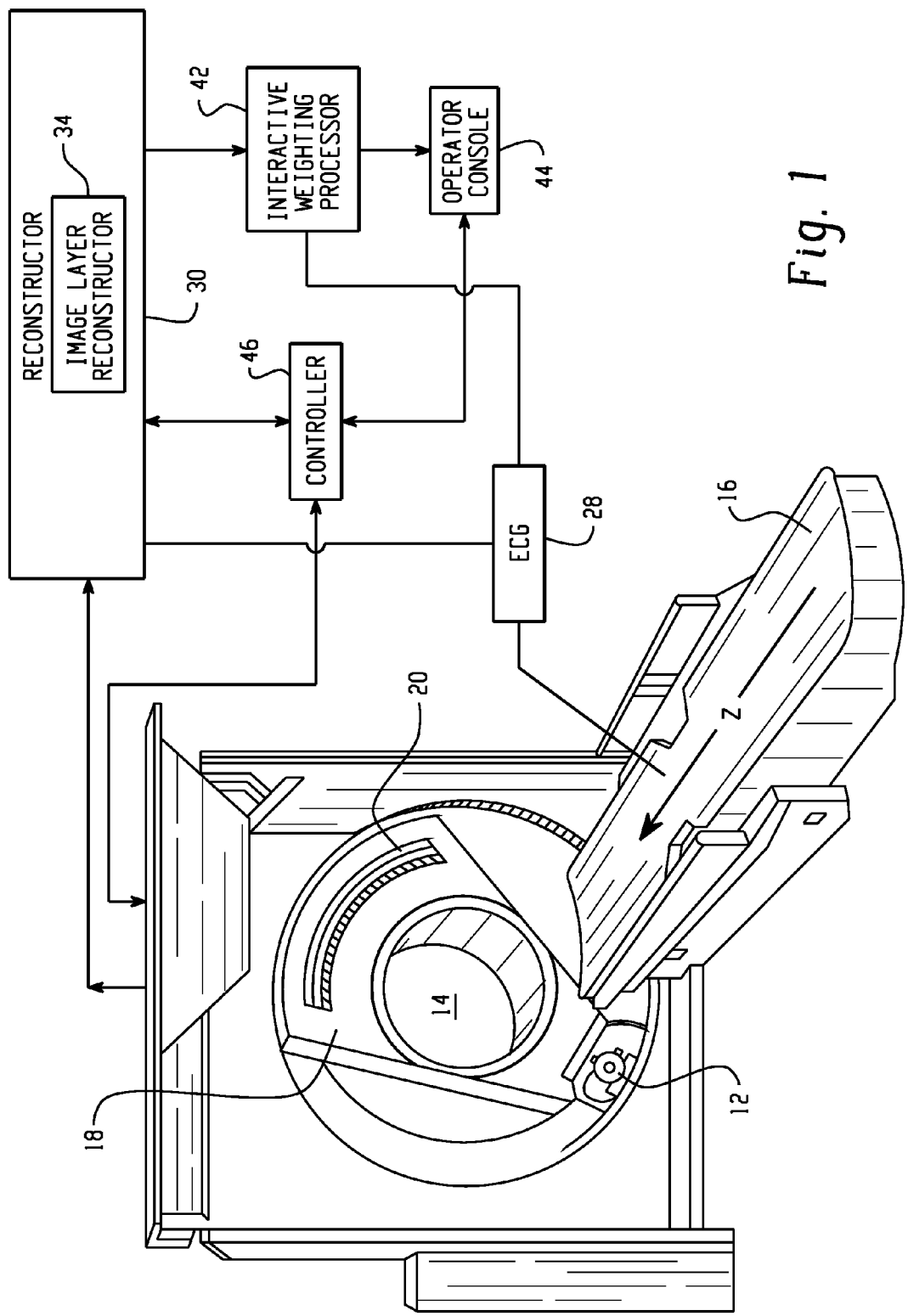
FIG. 1 depicts a CT scanner.

With reference to FIG. 1, a CT scanner 10 includes a rotating gantry 18 which rotates about the z-axis. The gantry 18 supports an x-ray source 12 such as an x-ray tube which generates a generally conical radiation beam. The gantry 18 also supports an x-ray sensitive detector 20 which subtends an angular arc on the opposite side of an examination region 14. The detector 20 is preferably a multi-slice detector which includes multiple rows or slices of detector elements extending in the z-direction and multiple columns of detector elements extending in the transverse direction. The detector 20 generates output signals indicative of radiation received along plurality of rays. Flat panel or other detector 20 configurations, as well as fourth generation or other system geometries, may also be implemented.

An electrocardiogram (ECG) unit 28 generates data indicative of the cardiac phase of a patient undergoing examination.

A patient support 16 such as a couch supports the patient in the examination region 14. The patient support 16 is preferably movable in the z-direction. A controller 28 coordinates the various scan parameters as necessary to carry out a desired scan protocol, including x-ray source 12 parameters such as tube voltage and current. Movement of the support 16 is preferably coordinated with rotation of the gantry so as generate a generally helical scan path.

A reconstructor 30 reconstructs the stream of projection data to generate volumetric data indicative of the interior anatomy of the patient. As will be described more fully below, the reconstructor 30 includes an image layer reconstructor 34 which reconstructs a plurality of image segments or layers.

An interactive weighting processor 42 processes the volumetric image data generated by the reconstructor 30 for display in human readable form.

A general purpose computer serves an operator console 44. The console 44 includes a human readable output device such as a monitor or display and an input device such as a keyboard and mouse. The console 44 also includes program and data memory, including a relatively larger but lower speed disc memory and a relatively smaller, but relatively faster, random access memory (RAM). Software resident on the console allows the operator to control the operation of the scanner 10 by establishing desired scan protocols, initiating and terminating scans, viewing and otherwise manipulating the volumetric image data, and otherwise interacting with the scanner 10. Note that the interactive weighting processor 42 and the operator console may be implemented in the same general purpose computer.

Figure 2:
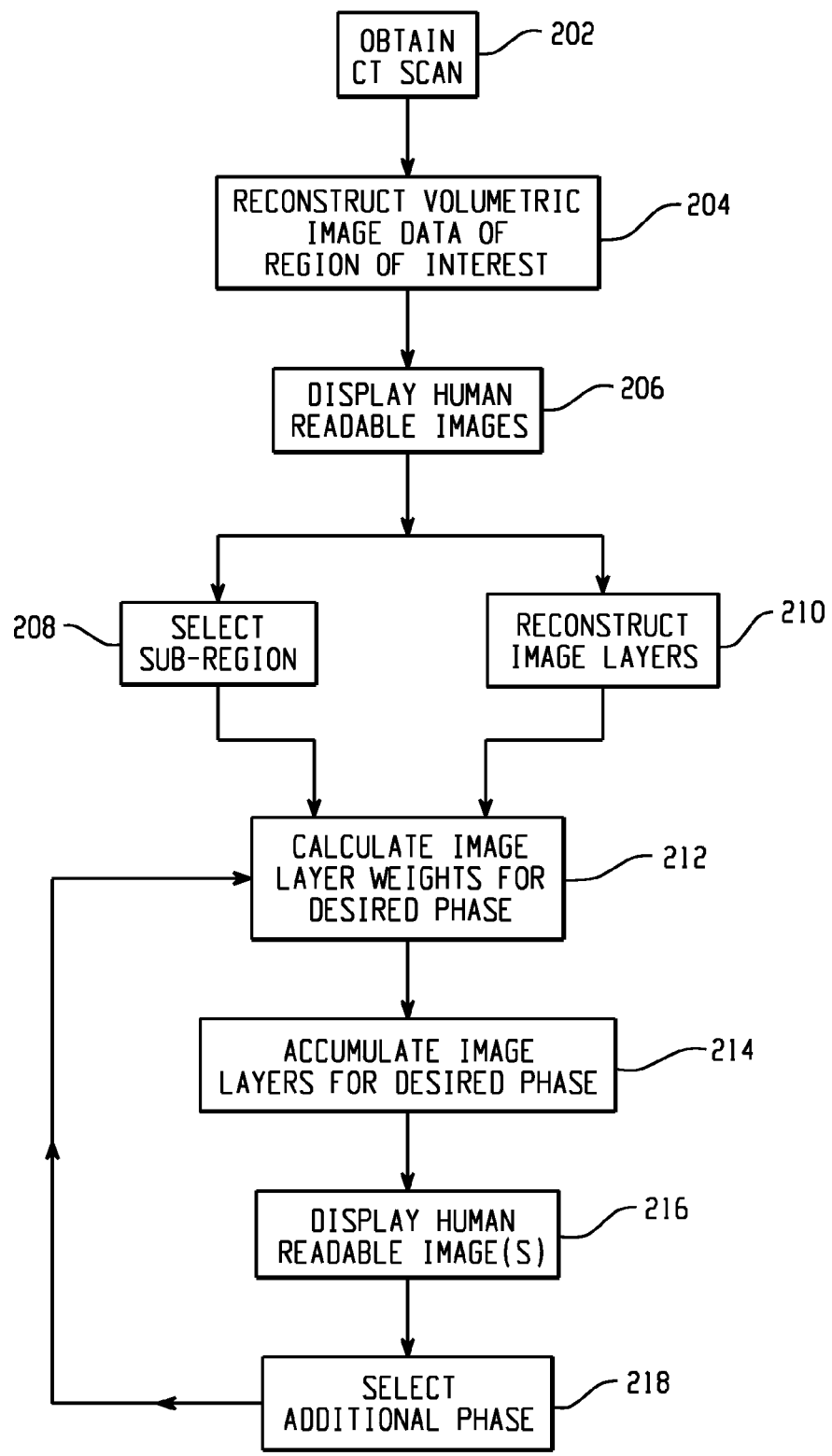
FIG. 2 depicts steps in an interactive visualization technique.

FIG. 2 depicts steps in a visualization technique which may be carried out using the scanner 10 and which is particularly well suited for the interactive visualization of periodically moving objects such as the coronary arteries of the heart.

At step 202, a CT scan of the patient is obtained. The patient's electrocardiogram (ECG) data is recorded along with the projection data.

At step 204, the reconstructor 30 reconstructs the projection data to generate volumetric data indicative of a volume or region of interest of the patient, for example a region which includes the heart. The ECG data is advantageously used to perform a retrospectively gated reconstruction at a desired phase of the patient's cardiac motion. As the volumetric data will be used in a subsequent step to identify a sub-region of interest, the reconstruction parameters may be established to generate images relatively quickly, albeit of a relatively lower quality. Alternately, the reconstruction parameters may be established to generate relatively higher, diagnostic quality data. In one implementation, the reconstruction is performed using the ECR method, although other suitable reconstruction techniques may be used.

At step 206, one more human readable images indicative of the volumetric data are displayed on the operator console 44. In one implementation, a region which includes the heart is presented as one or more 3D rendered images.

At step 208, the user selects a sub-region of interest. In the cardiac example, the user would ordinarily select sub-region of interest which contains one or more coronary arteries to be visualized in greater detail. As will be described more fully below, the maximum size of the sub-region selected by the user is preferably limited.

At step 210, the image layer reconstructor 34 performs a non-gated reconstruction of the projection data into a plurality of image segments or layers. More particularly, the projection data acquired during each rotation along the spiral path is divided in a plurality of projection segments having an angular displacement $\Delta\theta$:

$$\Delta\theta = \frac{2\pi}{Nseg} \qquad \text{Equation 1}$$

where Nseg is the number of segments per rotation. Note that Nseg may also be user adjustable. As will be described further below, each segment is convolved and backprojected over the region or sub-region of interest so as to form an image segment or layer.

The number of image layers NS to be backprojected can be estimated as follows:

$$NS \approx \frac{ST}{TS} \qquad \text{Equation 2}$$

where ST is the scan time and TS is the time shift between the projection segments that are used to generate successive image layers.

The size of the sub-region and the number of image layers are preferably established according to the relationship:

$$NS \cdot Nvoxels \cdot Svoxel < Smem \qquad \text{Equation 3}$$

where Nvoxels is the number of voxels in the sub-region, Svoxels is the number of bytes used to represent the value of each voxel in the sub-region, and Smem is the size of the console's RAM memory. Such an arrangement allows the sub-region of interest for each image layer to be loaded in the RAM memory of the console 44. As compared to situations in which some or all of the image layers are stored in the console 44 disc memory, such an arrangement will ordinarily allow the image layers to be processed much more quickly, if not substantially instantaneously from the perspective of a human user.

As one example, setting TS less than about 20 milliseconds (mS) can be expected to yield acceptable image quality in cardiac applications. A typical scan time of about 8 seconds (S) will thus result in about 400 image layers. Where the voxel values are stored as single precision floating point numbers, Svoxel is typically 4. Consequently, limiting the size of the sub-region to the range of $10^6$ voxels (i.e., in the range 64×64×64 voxels), which is reasonable for imaging of the coronary arteries, requires a RAM memory of about 1.6 GB. As will be appreciated, such a memory requirement is substantially less than would be required where the region of interest includes the entire image layer, which would typically be in the range of $10^8$ voxels (e.g., 512×512×512 voxels), and is within the range of RAM memory available for a typical computer.

At step 212, and as will also be described further below, the image layer weights are calculated for a desired cardiac phase.

At step 214, the image layers are accumulated or added according to the calculated weighting so as to generate volumetric image data indicative of the sub-region of interest at the desired cardiac phase. If the sub-region of interest for each of the desired image layers was not loaded into RAM memory prior to the calculation of the image weights 212, the information is loaded into RAM memory prior to the processing of the image layers.

At step 216, the volumetric image data indicative of the sub-region of interest at the desired phase is displayed in human readable form on the console 44 for review and/or further manipulation by the user.

If desired, the user may at step 218 select a different phase for review, and processing returns to step 212. A particular advantage to the foregoing arrangement is that, by storing only the sub-regions of interest of the various image layers in RAM, and by further avoiding backprojecting the volume with each change in cardiac phase, the processing of the image layers may ordinarily be performed substantially instantaneously from the viewpoint of a human user. Consequently, the phase selection and resultant visualization may be performed interactively.

One technique for generating and weighting the image layers according to the wedge method will now be described in relation to FIGS. 3 and 4. With reference to FIG. 3A, the projection data includes projection data $302_1 \ldots 302_n$ acquired at each of a plurality of positions about a generally helical scan trajectory 304.

At 402, and with reference to FIG. 3B, a fan beam to parallel beam rebinning is applied to the projection data 302 so as to generate a plurality of sets of projection data segments $306_1 \ldots 306_m$ containing equidistant parallel projections. Each projection data segment 306 is characterised by a starting angular position $\theta_m^{start}$ and an angular length $\Delta\theta$ selected as described above. Note that the adjacent data segments 306 are partially overlapped to facilitate transition weighting between successive image layers.

At 404, and with reference to FIG. 3C, the respective projection data segments $306_1 \ldots 306_m$ are weighted, convolved with a ramp filter, and backprojected to generate image layers $308_1 \ldots 308_m$. Each layer is characterized by a starting angular position $\theta_m^{start}$ and an angular displacement $\Delta\theta$ corresponding to that of its respective projection data segment 306.

As shown, each image layer 308 is angularly weighted according to a generally trapezoidal weighting function. The angular overlap and transition weighting is advantageously selected so that the sum of the weighting applied to adjacent image layers remains constant in the overlap regions 312.

At 406, the weighted image layers are then summed so as to generate the volumetric image data indicative of the sub-region of interest. Note that, in order to maximize the temporal resolution in a generated image, the summing is preferably limited to those image segments 308 which provide a complete CT data set (e.g., when combined, having an angular length of approximately $\pi$). The summation may also be performed over image segments 308 obtained at approximately the same point in multiple cardiac cycle. A particular advantage of the foregoing technique is that changing the desired phase requires a shifting along the image segments 308 which are accumulated to form the volumetric data. Compared to temporal rebinning of the projection data, such a technique avoids the necessity of performing a computationally expensive backprojection for each user-selected cardiac phase. Moreover, limiting image layers to sub-regions of a size which can be loaded into the relatively higher speed RAM memory of the console 44 facilitates the interactive visualization of different cardiac phases.

One drawback to the above technique, however, is that the cardiac phase can be shifted only in angular increments of $\Delta\theta$ (or stated another way, in the corresponding temporal increment). A technique which provides additional flexibility in selecting the phase will now be described in relation to FIGS. 5 and 6. The objective is to weight the image layers so that the projection-dependent weight profiles of each voxel within the sub-region of interest, obtained by taking into account the weight of each image layer and the weights of the projections used to construct each image layer, approximate those of a reference weighting function which can be readily calculated for an arbitrary phase point. As described below, this may be accomplished by weighting the image layers so as to approximate the weighting which would be obtained using the ECR method.

The patient's ECG is shown schematically at 502 for approximately three (3) cardiac cycles; an arbitrarily selected phase point of interest 504 is depicted in each of the cycles at $504_1, 504_2, 504_3$.

At step 602, a cardiac weighting function 506 is generated. The cardiac weighting function selects the projection data which corresponds temporally to the desired phase point 504. In one implementation, a $\cos^2$ weighting function is generated. Such a weighting function applies relatively larger weights to rays which are temporally near to the phase point and reaches zero at the gating window boundaries.

At step 604, an illumination weighting 508 is generated. The illumination window for a given voxel 510 is a function of the acquisition geometry and is characterized by angular positions $\theta_f$ and $\theta_l$ which define the respective first and last projection angles at which the voxel is illuminated. The illumination window may be calculated numerically for each voxel in the reconstruction volume. In one implementation, a trapezoidal weighting function is generated. The angular range defined by the illumination window determines the amount of redundant data available for each voxel in the reconstruction volume. The resulting multiple coverage within the illumination window is used in the cardiac weighting.

At 606, the cardiac 506 and illumination 508 weighting functions are multiplied to generate a combined weighting function 510.

At 608, the combined weighting function is 510 is normalized to generate a normalized weighting function 512 for each voxel or for blocks or groups of voxels. More particularly, the weighting functions are normalized with respect to all different $\pi$ partners. In the context of the ECR method, the normalized weighting function 512 would ordinarily be applied in the course of the backprojection. As described below, however, the normalized weighting function serves as a reference function which is used to calculate the weighting of the image layers.

At step 610, the image layers 308 which were generated only from projections which illuminate the voxel are identified.

At step 612, the weights for the identified image layers are calculated. More particularly, image layer weights are calculated to minimize the difference between the projection dependent weight profile of each voxel and the normalized weighting function 512 for that voxel. This may be accomplished by using a non-iterative closed-formula to calculate the difference, for example by minimizing the $l_2$ Hilbert space norm of the projection dependent difference At step 614, negative image layer weights are truncated to zero.

The image layer weights are normalized at step 616. More particularly, the image weights are normalized so that the sum of the weights for layers shifted in the acquisition stream by multiples of $\pi$ are equal to unity, or otherwise to a common value. Performing this normalization and selecting an angular displacement between successive image layers which divides well into the time of one-half of a gantry rotation insures that the sum of the weights given for all the projections used to reconstruct the voxel in the final image and belong to the same angle between 0 and $\pi$ will also equal unity. As is also known from the ECR method, the calculation of the image weights can be completed more quickly by calculating weights for regions or blocks of voxels, rather than calculating individual weights for each voxel.

Other variations are possible. As depicted in FIG. 4, the phase points 504 are shown as being at the same point in the cardiac cycle 502. However, the quality of the reconstructed image can be sensitive to variations in heart rate. Accordingly, the precise locations of the phase points $504_1$, $504_2$, $504_3$ within their respective cardiac cycles may be individually modified prior to calculation of the calculation of the temporal weighting function 506.

Thus, the user may be afforded to the opportunity to adjust one or more of the phase points $504_1$, $504_2$, $504_3$ relative to the cardiac cycle in a desired amount. The weighting functions are updated accordingly, and the updated images are generated and displayed interactively. As the weighting function may be adjusted in a substantially continuous fashion, the user is provided with additional flexibility to reduce the effects of perturbations in the cardiac cycle, which is further facilitated by the interactive nature of the process. As will be appreciated, such an arrangement facilitates the interactive optimization of image quality by allowing the user to interactively view the results of the modification and apply further modifications as desired.

While the foregoing has been described in connection with approximating reference functions which would be obtained using the ECR method, other desired reference weighting functions may also be used.

The invention has been described with reference to the preferred embodiments. Of course, modifications and alterations will occur to others upon reading and understanding the preceding description. It is intended that the invention be construed as including all such modifications and alterations insofar as they come within the scope of the appended claims.

The invention claimed is:

1. A method comprising:
   using projection data acquired during a tomographic examination of a periodically moving object to reconstruct a plurality of image layers, wherein the image layers are generated from projection data segments having an angular extent less than that which is required to provide a complete tomographic data set;
   generating a first reference weighting function which corresponds to the first motion phase;
   calculating image layer weights which minimize the difference between a projection dependent weight profile and the first reference weighting function for each of a plurality of regions in an image volume;
   weighting the image layers according to the calculated image layer weights so that the weighting applied to the image layers approximates the first reference weighting function;
   combining the image layers to generate first image data indicative of the object at an arbitrary first motion phase; and
   displaying a human readable image indicative of the first image data.

2. The method of claim 1 including: receiving an input from a human user indicative of an arbitrary second motion phase combining the image layers so as to generate second image data indicative of the object at the second motion phase; generating a human readable image indicative of the object at the second motion phase.

3. The method of claim 2 wherein the image layers are displaced by a first angular displacement and the first and second motion phases are separated by an angular distance which is less than the first angular displacement.

4. The method of claim 1 wherein combining includes combining image layers generated from projection data having a total angular length of approximately $\pi$.

5. The method of claim 1 wherein the object is a beating heart.

6. The method of claim 1 wherein generating the first weighting function includes: generating a temporally varying weighting function; generating an illumination window.

7. The method of claim 1 including reconstructing the projection data to generate third image data of a region of interest; selecting a sub-region of interest in the third image data; wherein the image layers correspond to the sub-region of interest.

8. The method of claim 1 wherein the first motion phase is established at a plurality of cycles of the object motion and including independently adjusting a phase point in at least one of the cycles; combining the image layers to generate fourth image data indicative of the object.

9. An apparatus comprising:
   means for using projection data acquired during a tomographic examination of a periodically moving object to reconstruct a plurality of image layers, wherein the image layers are generated from projection data segments having an angular extent less than that which is required to provide a complete tomographic data set;
   means for generating a first reference weighting function which corresponds to the first motion phase;
   means for calculating image layer weights which minimize the difference between a projection dependent weight profile and the first reference weighting function for each of a plurality of regions in an image volume;
   means for weighting the image layers according to the calculated image layer weights so that the weighting applied to the image layers approximates the first reference weighting function;
   means for combining the image layers to generate first image data indicative of the object at an arbitrary first motion phase; and
   means for displaying a human readable image indicative of the first image data.

10. A method comprising:
   using projection data acquired during a CT examination of a periodically moving object to reconstruct a plurality of image layers, wherein the image layers are generated from a plurality of angularly displaced projection data segments;

calculating a first image layer weight and second image layer weight which minimize the difference between a projection dependent weight profile and the first reference weighting function for each of a plurality of regions in an image volume;

combining the image layers according to a first weighting function that includes the first image layer weight to generate first image data indicative of the object at a first motion phase;

displaying a human readable image indicative of the first image data;

combining the image layers according to a second weighting function that includes the second image layer weight so as to generate second image data indicative of the object at a second motion phase; and generating a human readable image indicative of the object at the second motion phase; wherein the image layers are displaced by a first angular displacement and wherein the first and second motion phases are separated by an angular distance which is less than the first angular displacement.

11. The method of claim 10 including: generating a cardiac weighting function percentage for the first motion phase; generating an illumination weighting function; combining the cardiac and illumination weighting functions to generate a combined weighting function; normalizing the combined weighting function to generate a normalized weighting function.

12. The method of claim 10 wherein the first weighting function weights the Image layers so that the projection dependent weight profiles of a plurality of regions within an image region approximate those of a reference weighting function.

13. The method of claim 12 wherein the projection data is x-ray CT data acquired along a spiral path and including dividing the projection data acquired during each rotation along the spiral path into a plurality of projection segments.

14. The method of claim 10 including reconstructing the projection data to generate image data indicative of a region of interest of the object; displaying the image data in human readable form; receiving an input from human user indicative of a sub-region of interest of the object; wherein the step of using projection data is performed temporally in parallel with the step of receiving an input.

15. A non-transitory computer readable storage medium which carries instructions which, when executed by a computer, cause the computer to carry out a method comprising:

using projection data acquired during a tomographic examination of a periodically moving object to generate a plurality of image layers;

generating a first angularly varying reference weighting function;

calculating image layer weights according to the first angularly varying reference weighting function which minimizes the difference between a projection dependent weight profile and the first reference weighting function for a plurality of regions in an image volume; wherein weighting the image layers includes weighting the image layer according to the calculated weights;

weighting the image layers according to the calculated image layer weights so that the weighting applied to the image layers approximates the first weighting function;

combining the weighted image layers to generate first volumetric data indicative of the object; and generating a human readable image indicative of the first volumetric data.

16. The computer readable storage medium of claim 15 wherein the method includes generating a second angularly varying reference weighting function; weighting the image layers so that the weighting applied to the image layers approximates the second reference weighting function; combining the weighted image layers to generate second volumetric data indicative of the object.

17. The computer readable storage medium of claim 16 wherein the first reference function corresponds to a first phase of the periodic motion and the second reference function corresponds to a second phase of the periodic motion.

18. The computer readable storage medium of claim 15 wherein combining includes combining image layers having a total angular length of approximately $\pi$.

19. The computer readable storage medium of claim 15 wherein generating the first reference weighting function includes: generating a temporal weighting function; generating an illumination window for each of a plurality of regions in a reconstruction volume.

20. The computer readable storage medium of claim 15, wherein the method includes reconstructing the projection data to generate third volumetric data of a region of interest; selecting a sub-region of interest in the third volumetric data; wherein the partial image layers correspond to the sub-region of interest.

* * * * *